(12) United States Patent
Nobile et al.

(10) Patent No.: US 11,077,442 B2
(45) Date of Patent: Aug. 3, 2021

(54) APPARATUS AND METHOD FOR EXTRACTING PATHOGENS FROM BIOLOGICAL SAMPLES

(71) Applicant: Tangen Bioscience Inc., Branford, CT (US)

(72) Inventors: John Richard Nobile, Guilford, CT (US); John F. Davidson, Guilford, CT (US)

(73) Assignee: TANGEN BIOSCIENCES, INC., Branford, CT (US)

(*) Notice: Subject to any disclaimer, the term of this patent is extended or adjusted under 35 U.S.C. 154(b) by 0 days.

(21) Appl. No.: 16/805,195

(22) Filed: Feb. 28, 2020

(65) Prior Publication Data

US 2020/0368743 A1   Nov. 26, 2020

Related U.S. Application Data

(63) Continuation of application No. 15/471,154, filed on Mar. 28, 2017, now Pat. No. 10,625,263.

(Continued)

(51) Int. Cl.
*B01L 1/00* (2006.01)
*B01L 3/00* (2006.01)
(Continued)

(52) U.S. Cl.
CPC ......... *B01L 3/50825* (2013.01); *B01L 3/5023* (2013.01); *C12Q 1/24* (2013.01); *G01N 1/14* (2013.01); *G01N 1/4077* (2013.01); *B01L 2200/0689* (2013.01); *B01L 2200/16* (2013.01); *B01L 2300/046* (2013.01); *B01L 2300/047* (2013.01); *B01L 2300/0672* (2013.01); *B01L 2300/0681* (2013.01); *B01L 2300/0832* (2013.01); *B01L 2300/123* (2013.01); *B01L 2400/0478* (2013.01);
(Continued)

(58) Field of Classification Search
None
See application file for complete search history.

(56) References Cited

U.S. PATENT DOCUMENTS 3,767,085 A   10/1973   Cannon et al.
4,261,474 A   4/1981   Cohen
(Continued)

FOREIGN PATENT DOCUMENTS

DE   102006032637 A1   1/2008

OTHER PUBLICATIONS

International Search Report and Written Opinion dated Apr. 1, 2016 for PCT Application No. PCT/US15/058612.
(Continued)

*Primary Examiner* — Jyoti Nagpaul
(74) *Attorney, Agent, or Firm* — Spectrum IP Law Group LLC (57) ABSTRACT

The disclosed embodiments related to an apparatus and methods for biological sample processing enabling isolation and concentration of microbial or pathogenic constituents from the sample. Sample may be obtained directly from a specimen container, such as a vacutainer, and processed directly without risk of user exposure. The disclosed methods and apparatus provide a convenient and inexpensive solution for rapid sample preparation compatible with downstream analysis techniques.

12 Claims, 7 Drawing Sheets

Related U.S. Application Data (60) Provisional application No. 62/313,985, filed on Mar. 28, 2016.

(51) Int. Cl.
    *G01N 1/40*     (2006.01)
    *C12Q 1/24*     (2006.01)
    *G01N 1/14*     (2006.01)

(52) U.S. Cl.
    CPC ............... *B01L 2400/0487* (2013.01); *B01L 2400/0605* (2013.01); *B01L 2400/0638* (2013.01); *B01L 2400/0683* (2013.01); *B01L 2400/0694* (2013.01); *G01N 2001/4088* (2013.01)

(56) References Cited

U.S. PATENT DOCUMENTS

| | | | |
|---|---|---|---|
| 5,693,233 | A | 12/1997 | Schembri |
| 6,686,195 | B1 | 2/2004 | Colin et al. |
| 2002/0187547 | A1 | 12/2002 | Taylor et al. |
| 2005/0182383 | A1 | 8/2005 | Wallen |
| 2006/0013732 | A1 | 1/2006 | Parthasarathy et al. |
| 2008/0103297 | A1 | 5/2008 | Parthasarathy et al. |
| 2008/0114304 | A1 | 5/2008 | Nalesso et al. |
| 2010/0086990 | A1 | 4/2010 | Stanley et al. |
| 2010/0147402 | A1 | 6/2010 | Tornqvist |
| 2010/0286513 | A1 | 11/2010 | Pollard, Jr. et al. |
| 2010/0290955 | A1 | 11/2010 | Cho et al. |
| 2011/0009837 | A1 | 1/2011 | Schreiner |
| 2014/0031772 | A1 | 1/2014 | Hardy et al. |
| 2014/0120599 | A1 | 5/2014 | Daub et al. |
| 2015/0073348 | A1* | 3/2015 | Bullington ....... A61B 5/150389 604/187 |

OTHER PUBLICATIONS

International Search Report and Written Opinion dated Apr. 29, 2014 for PCT Application No. PCT/US13/075430.

International Search Report and Written Opinion dated Jul. 27, 2017, to PCT Application No. PCT/US2017/24455.

Ralf Himmelreich, "Device for the information of biological samples e.g. cells/tissues, comprises sound producing mechanism, which produces sound wave in the sample to be treated, a reception for a container, mixer with a retainer for mix element, and drive" DE102006032637, Jan. 17, 2008 [English translation of Abstract].

\* cited by examiner

APPARATUS AND METHOD FOR EXTRACTING PATHOGENS FROM BIOLOGICAL SAMPLES

The instant disclosure is a continuation application of and claims priority under 35 U.S.C. § 120 to U.S. patent application Ser. No. 15/471,154, filed Mar. 28, 2017 which in turn claims priority to Provisional Application No. 62/313,985, filed Mar. 28, 2016, the specifications of which are incorporated herein in their entirety.

FIELD OF THE DISCLOSURE

The disclosure is directed generally to apparatus and methods for biological sample processing including obtaining selected materials from a biological sample. More specifically, the disclosure relates to an apparatus and methods for isolating and concentrating microorganisms of interest from a biological sample such as blood, sputum, or cerebrospinal fluid.

BACKGROUND

Rapid isolation and collection of microorganisms, such as pathogenic bacteria, from biological samples is an important aspect to clinical evaluation and testing. Accurate diagnosis and pathogen monitoring may involve obtaining a sample from a subject, for example, in the form of sputum, blood, tissue, urine, cerebrospinal fluid or other biological specimen. Extraction techniques may then be used to isolate and concentrate pathogens from the specimen. In some instances, intact pathogens may be desirably collected for culture or analysis while other approaches may enrich for nucleic acids, proteins or other biological indicators used to detect or identify the presence of a pathogen or infectious agent within the sample.

Conventional methods for collecting microorganisms from a biological sample are typically slow and lack the ability to readily isolate and separate small quantities of pathogens from larger sample volumes in which they are contained. Blood-based processing techniques may require centrifugation and withdrawal of sub-fractions from the sample to obtain crude pathogen isolates. In some conventional processing workflows, technicians must work with open sample containers and perform transfer operations manually creating potential biological and exposure hazards.

A particular problem exists when attempting to extract and analyze pathogens from biological samples where the overall amount of the sample is large or where the number of pathogens present is very small. In such circumstances, conventional processing techniques may not be able to efficiently concentrate and retain the microorganisms in a manner suitable for rapid identification. In these and other regards, the present disclosure provides significant advances in sample processing and analysis techniques that facilitate and improve microorganism isolation and identification.

SUMMARY OF THE DISCLOSURE

According to various embodiments, an apparatus and methods for rapid isolation, concentration, and purification of microbes/pathogens of interest from a raw biological sample such as blood is described. Samples may be processed directly from biological or clinical sample collection vessels, such as vacutainers, by coupling with the sample processing apparatus in such a manner that minimizes or eliminates user exposure and potential contamination issues.

In various embodiments, the apparatus comprises a staged syringe or piston arrangement configured to withdraw a desired quantity of biological sample from a sample collection vessel. The sample is then mixed with selected processing reagents preparing the sample for isolation of microbes or pathogens contained therein. Sample processing may include liquefying or homogenizing non-pathogenic components of the biological specimen and performing various fluidic transfer operations induced by operation of the syringe or piston. The resulting sample constituents may be redirected to flow across a capture filter or membrane of appropriate size or composition to capture specific microbes/pathogens or other biological sample constituents. Additional operations may be performed including washing and drying of the filter or membrane by action of the syringe or piston. In various embodiments, sample backflow and cross-contamination within the device is avoided using one-way valves that direct sample fluids along desired paths while preventing leakage, backflow, and/or undesired sample movement.

The device may include a capture filter for retaining microbes/pathogens of interest allowing them to be readily separated from sample eluent or remaining fraction of the processed sample/waste. The capture filter may be housed in a sealable container and can further be configured to be received directly by other sample processing/analytical instruments for performing downstream operations such as lysis, elution, detection and identification of the captured microbes/pathogens retained on the filter/membrane.

The collector may comprise various features to facilitate automated or semi-automated sample processing and include additional reagents contained in at least one reservoir integrated into the collector to preserve or further process the isolated microbes/pathogens captured or contained by the filter/membrane. In various embodiments, the collector may contain constituents capable of chemically disinfecting the isolated microbes/pathogens or render the sample non-infectious while preserving the integrity of biological constituents associated with the microbe/pathogen such as nucleic acids and/or proteins that may be desirably isolated for subsequent downstream processing and analysis. The collector and associated instrument components may desirably maintain the sample in an isolated environment avoiding sample contamination and/or user exposure to the sample contents.

In various embodiments, this present disclosure describes an apparatus that permits rapid and semi-automated isolation and extraction of microorganisms such as bacteria, virus, spores, and fungi or constituent biomolecules associated with the microorganisms, such as nucleic acids and/or proteins from a biological sample without extensive hands-on processing or lab equipment. The apparatus has the further benefit of concentrating the microbes, pathogens, or associated biomolecules/biomaterial of interest. For example, bacteria, virus, spores, or fungi present in the sample (or nucleic acids and/or proteins associated therewith) may be conveniently isolated from the original sample material and concentrated on the filter or membrane. Concentration in this manner increases the efficiency of the downstream assays and analysis improving detection sensitivity by providing lower limits of detection relative to the input sample.

The sample preparation apparatus of the present disclosure may further be adapted for use with analytical devices and instruments capable of processing and identifying the microorganisms and/or associated biomolecules present within the biological sample. In various embodiments, the sample collector and various other components of the system can be fabricated from inexpensive and disposable materials such as molded plastic that are compatible with downstream sample processing methods and economical to produce. Such components may be desirably sealed and delivered in a sterile package for single use thereby avoiding potential contamination of the sample contents or exposure of the user while handling. In various embodiments, the reagents of the sample collector provide for disinfection of the sample constituents such that may be disposed of without risk or remaining infectious or hazardous. The sample collector provides simplified workflows and does not require specialized training or procedures for handling and disposal.

In various embodiments, the automated and semi-automated processing capabilities of the system simplify sample preparation and processing protocols. A practical benefit may be realized in an overall reduction in the number of required user operations, interactions, or potential sample exposures as compared to conventional sample processing systems. This results in lower user training requirements and fewer user-induced failure points. In still other embodiments, the system advantageously provides effective isolation and/or decontamination of a sample improving overall user safety while at the same time preserving sample integrity, for example by reducing undesirable sample degradation.

Additional objects and advantages of the disclosed embodiments will be set forth in part in the description that follows, and in part will be apparent from the description, or may be learned by practice of the disclosed embodiments. It is to be understood that both the foregoing general description and the following detailed description are exemplary and explanatory only and are not restrictive of the scope of disclosed embodiments.

BRIEF DESCRIPTION OF THE DRAWINGS

These and other embodiments of the disclosure will be discussed with reference to the following exemplary and non-limiting illustrations, in which like elements are numbered similarly, and where.

DETAILED DESCRIPTION

Figure 1:
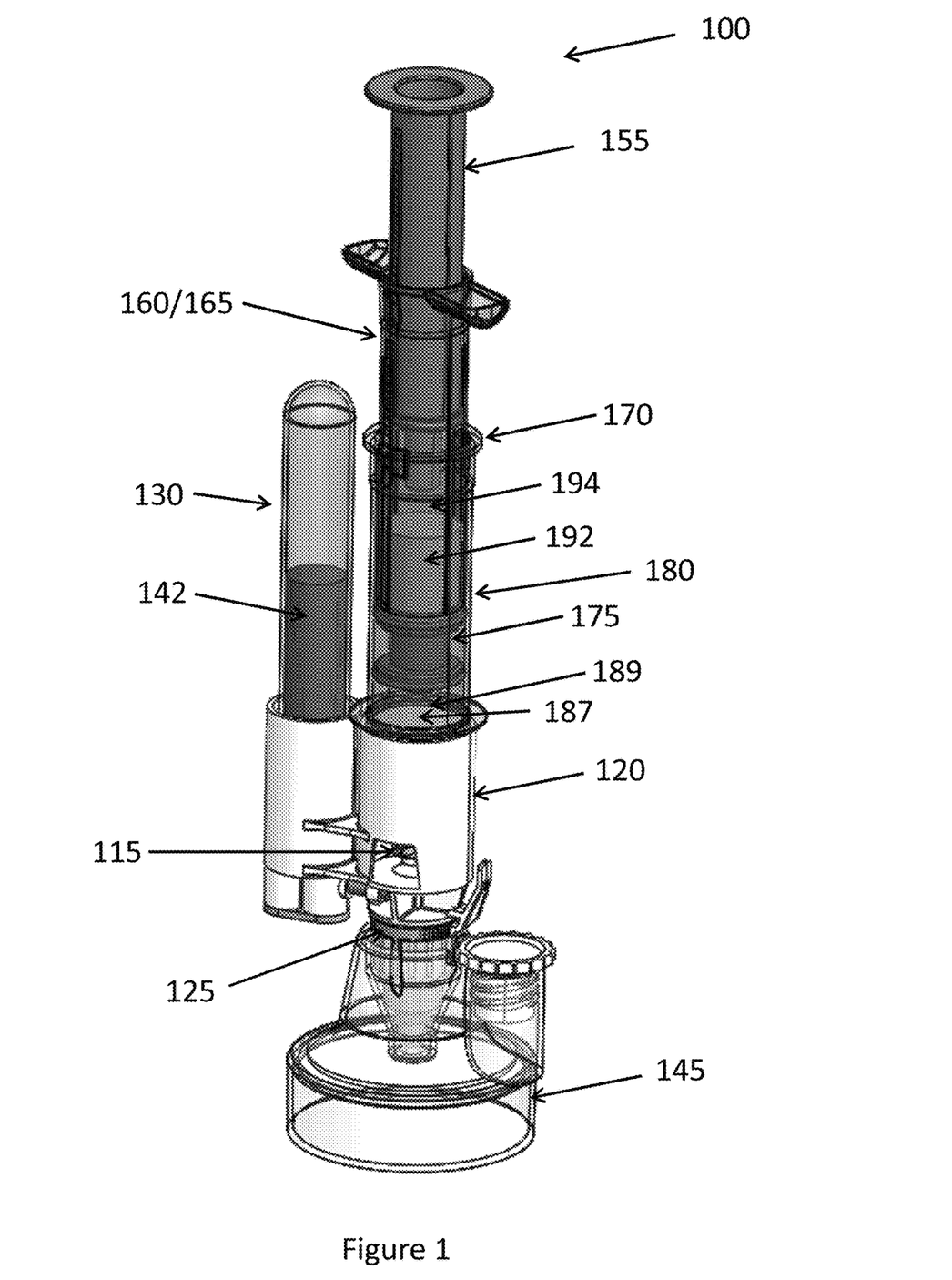
FIG. 1 illustrates an exemplary embodiment of the sample processing apparatus of the disclosure.
Figure 4A:
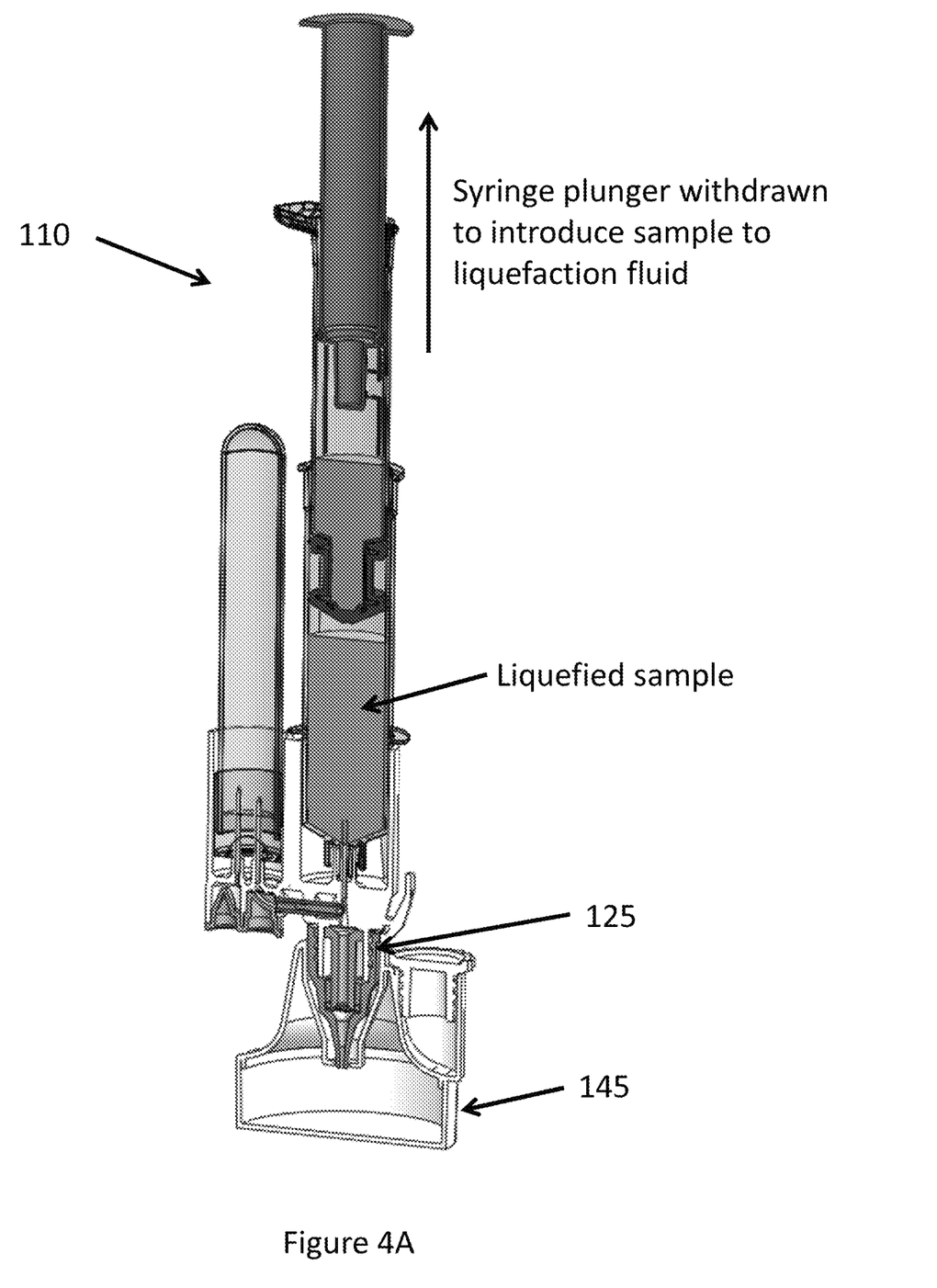
FIG. 4A illustrates a first step in an exemplary process where the plunger is withdrawn to introduce relative negative pressure in the sample tube.

An illustration of one embodiment of the sample processing apparatus 100 of the present disclosure is depicted in FIG. 1. The apparatus 100 may be configured with a multi-stage syringe 110 FIG. 4A) having an outlet that mates or joins with a syringe coupler 115 provided on a valve body 120. The valve body 120 is further configured to mate or join with a capture tube or reservoir 125 and a sample tube or reservoir 130 via capture tube coupler 135 and sample tube coupler 140 respectively. As will be described in greater detail hereinbelow the valve body 120 comprises a sample delivery assembly having one or more valves and sample flow paths that allow sample 142 contained in a sample collection tube 130 to be withdrawn and distributed by operation of the syringe 110.

Figure 2:
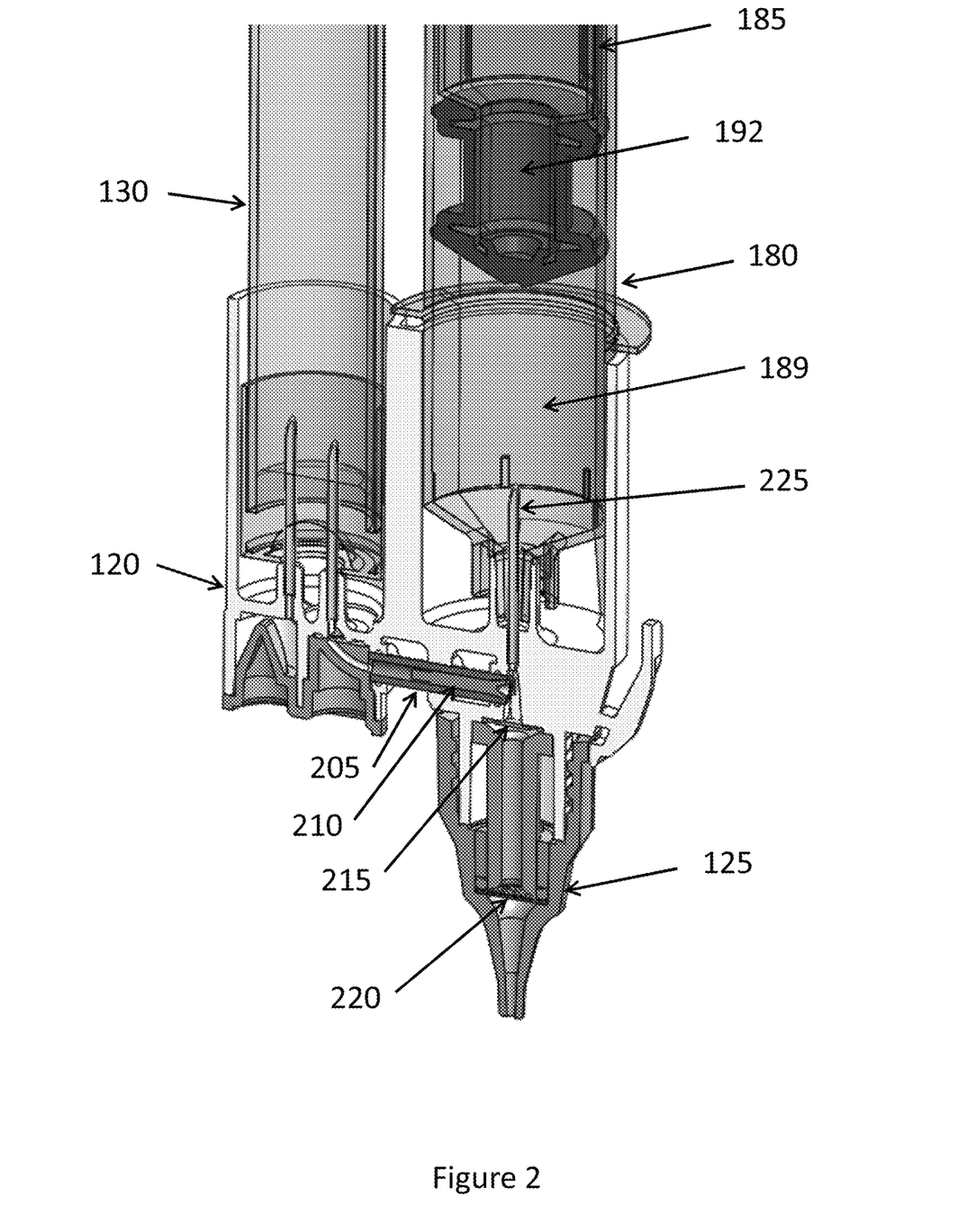
FIG. 2 illustrates an expanded cross-sectional view of the valve body for an exemplary sample processing apparatus of the disclosure.

In various embodiments, the syringe 110 may comprise a two-stage assembly having an inner plunger/piston 155 and inner barrel 160. The inner barrel 160 may also serve as or be associated with an outer plunger/piston 165 that operates in connection with an outer barrel 170. The outer barrel 170 mates with the valve body 120 by the syringe coupler 115 such that sample 142 may be drawn into the barrel 170. A first plunger tip or gasket 175 separates an outer barrel reservoir 180 from and inner barrel reservoir 185 (FIG. 2). Each reservoir 180, 185 may contain various reagents and components used in sample processing.

With simultaneous reference to FIGS. 1 and 2, the outer barrel reservoir 180 may contain a first processing fluid such as a liquefaction reagent 187 (FIG. 1) selected based on the sample type and when mixed with the sample 142 may result, for example, in breaking down selected constituents of the sample 142. The constituents may include blood cells, sputum, or other components that are to be made to desirably pass through the capture tube 125 without being retained such that they may be separated from microbes/pathogens which will be retained by the capture tube 125. The liquefaction fluid 187 may be preloaded in the reservoir 180 in a predetermined quantity such that the apparatus 100 is made ready-to-use requiring little or no significant preparation before introduction of the sample 142. The reservoir 180 may further be sized to accommodate a selected volume of liquefaction fluid 187 and additionally provide an air volume 189. As will be described in greater detail, providing a selected volume of air 189 facilitates sample processing such as mixing and sample distribution to other components within the apparatus 100.

The inner barrel reservoir 185 may contain a second processing fluid such as a wash reagent 192 used to further process the sample 142. Similar to the first processing fluid 187, the second processing fluid 192 may be preloaded in the reservoir 185 in a predetermined quantity. The reservoir 185 may also be sized to accommodate a selected volume of air 194 facilitating sample processing and distribution.

By operation of the plunger 165, sample 142 may be drawn from the sample tube 130 through the valve body 120 and introduced into the outer reservoir 180 where it is mixed with the first processing fluid 187. The resulting mixture may then be expelled through the capture tube 125 into the waste receptacle 145. As part of this operation, microbes/pathogens released or present in the sample 142 may be captured and retained on a filter/membrane (not shown in FIG. 1) associated with the capture tube 125 thereby separating them from the rest of the processed sample. A desirable aspect of this approach, is that significant volumes of sample can be passed through the capture tube 125 retaining microbes/pathogens contained therein and effectively concentrating or localizing them on the filter/membrane.

The volume of air 189 contained in the reservoir 170 can then be made to pass over the filter and retained microbes/ pathogens to aid in removing residual first processing fluid 187 and efficiently expelling into the waste reservoir 145. As will be described in greater detail, the air volume 189 may also provide separation between additional processing steps where the second processing fluid 192 is exposed to the sample constituents including the microbes/pathogens retained on the filter/membrane.

FIG. 2 illustrates an expanded cross-sectional view of the valve body 120 for the sample processing apparatus 100. Channels 205 fluidically connect the sample tube 130 with the syringe 110 and the capture tube 125. According to various embodiments, fluidic restrictors or one way valves 210, 215 may be provided that moderate and direct the flow of sample and fluid within the channels 205. These valves 210, 215 may comprise a diaphragm or other device that prevents backflow into a particular component of the assembly 100. For example, the sample tube valve 210 may permit sample (e.g. blood) to be drawn from the sample tube 130 into selected channels 205 when the plunger 155 is actuated in a first direction (e.g. fluid draw). Sample passes through the channels 205 and into the syringe reservoir 180 where it may mix with the first processing reagent 187. The one-way capture tube valve 215 may prevent or restrict entry of fluid into the capture tube 125 during the sample fluid draw stage from the sample tube 130.

Subsequent actuation of the inner barrel/outer plunger 160, 165 in a second direction (e.g. fluid push) may result in the one-way valve 210 associated with the sample tube 130 remaining closed thereby preventing fluid flow into the sample tube 130. Substantially simultaneously, the one-way valve 215 associated with the capture tube 125 may permit fluid flow into the capture tube 125 allowing processed sample (e.g. sample mixed with processing fluid) to pass through a filter/membrane 220 used to separate microbes/pathogens from the remainder of the sample eluent.

According to various embodiments, a needle or piercing member 225 may be positioned in a manner to allow penetration of the gasket 175 creating a fluidic interconnection between the first and second reservoirs 180, 185. Operation of the outer plunger 165 may thus first draw sample 142 from the sample tube 130 into the first reservoir 180 and upon expulsion of the sample/first processing fluid mixture through the capture tube 125 position the gasket 175 such that it engages with the piercing member 225 creating a hole or channel in the gasket 175. Second processing fluid 192 may then be introduced into the channels 205 by operation of the inner plunger 155 which expels the second processing fluid 192 from the second reservoir 185 either into the first reservoir 180 or directly into the channels 205.

As previously noted, the air volume 189 present in the first reservoir creates a gap that permits the first processing fluid 187 to be substantially or completely expelled from the first reservoir 180 prior to piercing of the gasket 175 and entry of the second processing fluid 192 into the first reservoir 180 and/or channels 205. Such a configuration may be desirable to maintain separation between the two processing fluids 187, 192 and provides a means by which to conduct substantially different steps or treatments on the sample and/or retained microbes. For example, the first processing fluid 187 may be used to liquefy the sample breaking it down into a form that allows passage through the filter 220 while the second processing fluid 192 may be subsequently introduced as a wash, preservative, or lysis agent for the microbes/pathogens retained on the filter 220.

It will be appreciated that the configuration of the apparatus 100 desirably provides a closed or sealed environment for sample processing. Sample can be conveniently withdrawn from the sample tube 130 and a series of one or more processing steps conducted using the sample 142 with various processing fluids 187, 192 without having to individually handle or measure the fluidic components. Operation of the assembly 100 may further be conducted manually or using an instrument or apparatus configured to impart desired mechanical drawing and pushing forces on the plunger(s) 155, 165. The resulting filter 220 containing isolated microbes as well as the capture sample eluent retained in the reservoir 145 may be used in further operations, processing steps, and analysis.

Figures 3A, 3B:
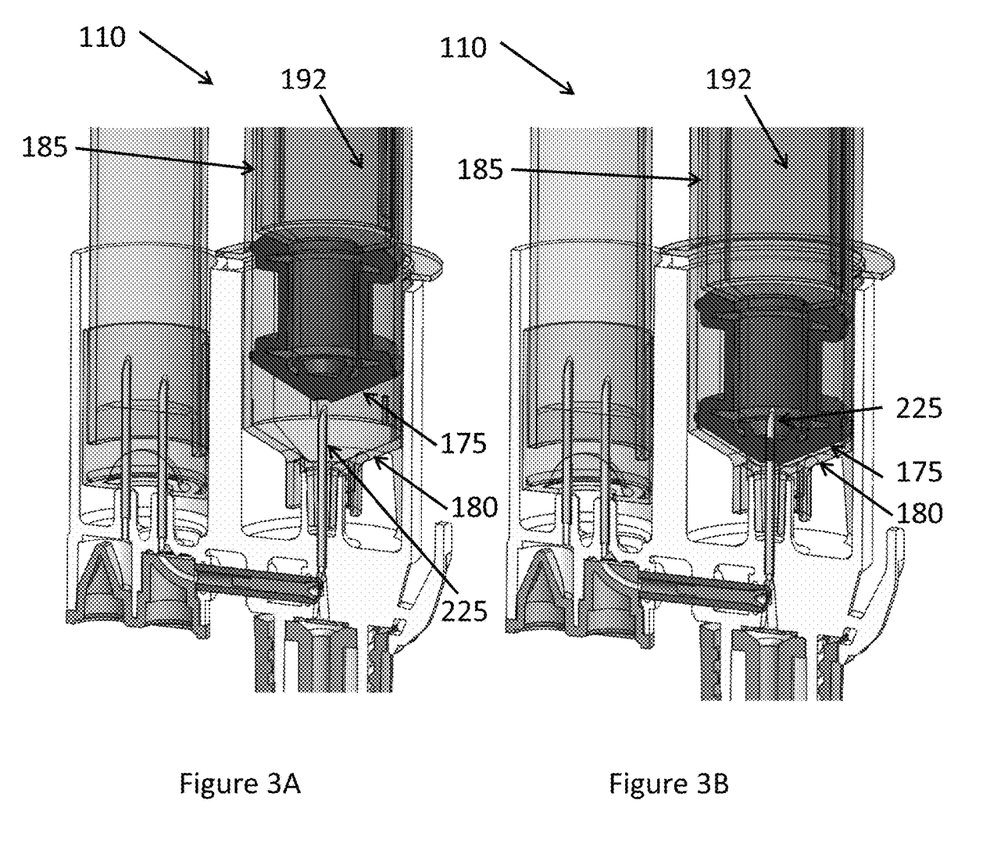
FIG. 3A illustrates detail view for a piercing member and an exemplary first position to provide an automatic or predetermined multi-stage fluidic release capability according to one embodiments of the disclosure.
FIG. 3B illustrates detail view for a piercing member and an exemplary second position to provide an automatic or predetermined multi-stage fluidic release capability according to one embodiments of the disclosure.

FIG. 3AB illustrate further detail views for the needle or piercing member 225 and exemplary positioning and penetration of the gasket 175 to provide an automatic or predetermined multi-stage fluidic release capability for the syringe 110. FIG. 3A illustrates exemplary positioning of the needle 225 prior to piercing the seal/gasket 175. As indicated, the reservoirs 180, 185 and processing reagents 187, 192 are maintained separately before penetration of the gasket 175. The first processing reagent 187 may further interact with the sample 142 and be expelled from the syringe 110.

As shown in FIG. 3B, actuation or displacement of the plunger 165 is then conducted sufficient to engage the needle 225 with the gasket 175 resulting in piercing of the seal 175 and permitting the second processing fluid 192 to enter through the newly created channel. In various embodiments, the needle 225 includes a channel extending through its length for fluid passage, however, the fluid may also be allowed to escape or pass around the piercing member 225 into the first reservoir 180 directly. Further actuation or displacement of the inner plunger 155 (not shown in FIG. 3) permits the second processing fluid 192 to be expelled from the inner reservoir 185.

FIGS. 4A-D illustrate operation of the sample processing apparatus 100. As indicated by the arrows depicting fluidic movement in the valve body of FIG. 4A, sample may be withdrawn from the sample tube, pass through the one or more channels and mix with the first processing reagent in the syringe reservoir. The first processing reagent may react or interact with the sample to achieve a desired state or composition. For example, as shown in the figure, mixing of sample with the first processing reagent results in the formation of a liquefied sample suitable for passage through the sample collector. Exemplary operation of the plunger in a draw direction as indicated by the arrow in FIG. 4A introduces the sample to liquefaction fluid.

Figure 4B:
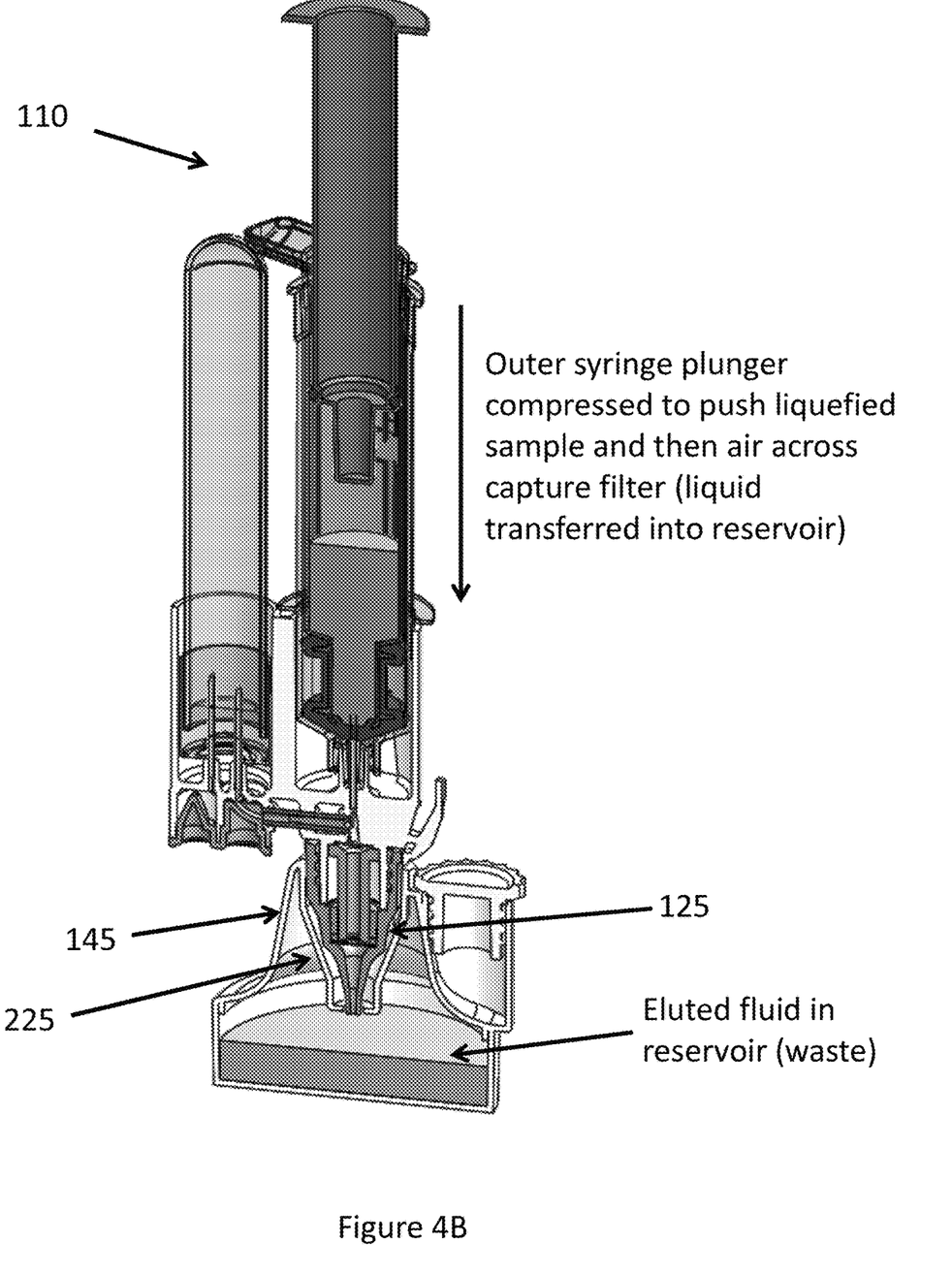
FIG. 4B illustrates a second step in an exemplary process where the plunger is compressed to introduce relative positive pressure in the reservoirs.

As shown in FIG. 4B, upon suitable mixing of sample and first processing fluid, the mixture may be expelled or passed through the capture tube by compression or actuation of the outer plunger. The capture filter provides a desired surface or medium by which to retain and concentrate selected components of the processed sample. For example, microbes/pathogens may be retained on a filter or membrane having suitable porosity or molecular composition to permit passage of the processed liquid sample while selectively capturing microorganisms or other desired sample constituents.

Figure 4C:
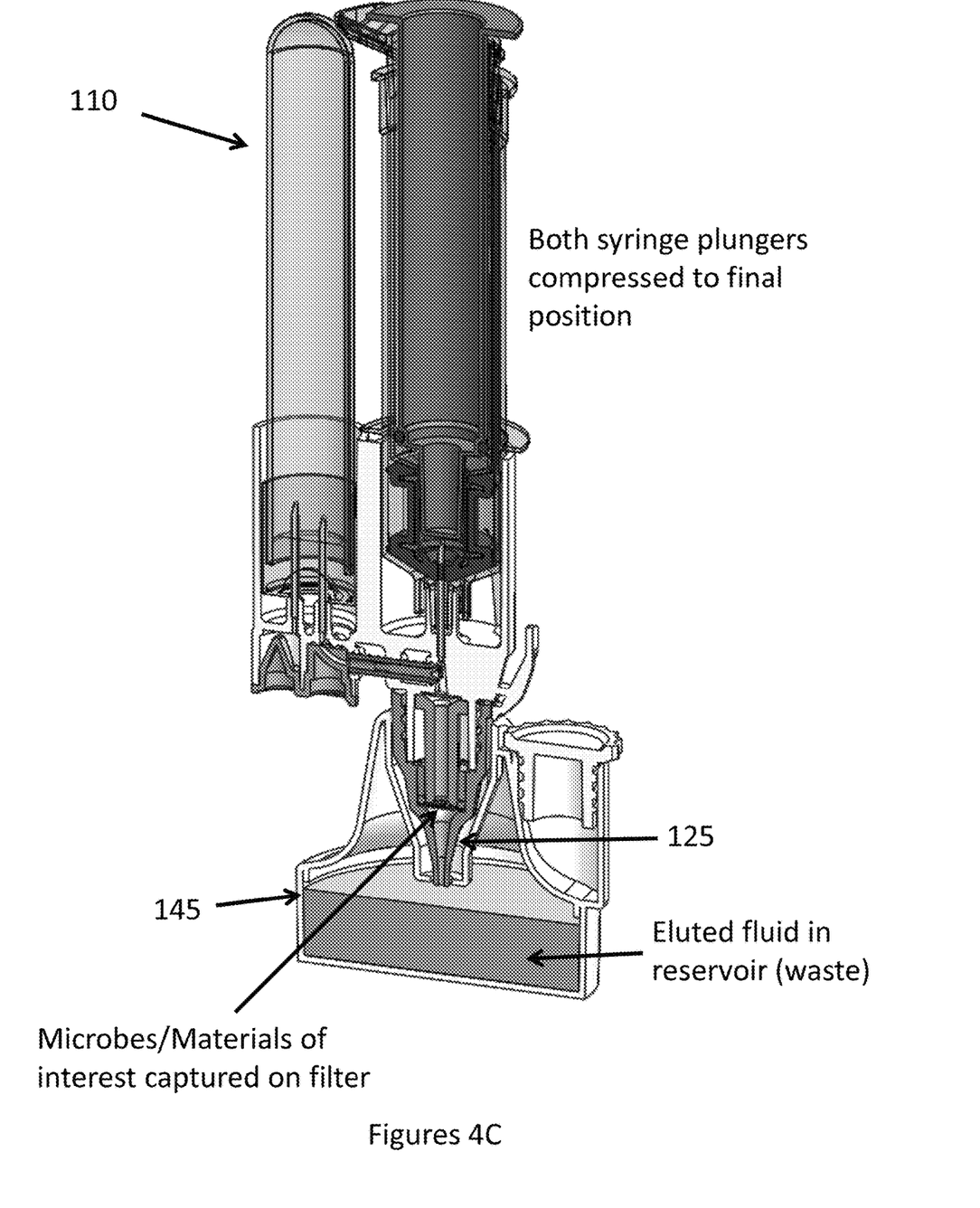
FIG. 4C illustrates a third step in an exemplary process where the syringe is compressed into a final position.

As shown in FIG. 4C, further compression or actuation of the inner plunger engages the needle with the gasket and releases the second processing fluid into the channels of the valve body. The second processing fluid release may be preceded by a flow of air through the channels resultant from the air volume contained in the first reservoir aiding in purging the first fluidic mixture from the assembly and further improving the capture or retention of desired sample constituents on the filter or membrane. Fully compressing the inner plunger purges the second processing fluid from the inner reservoir and permits its interaction with the retained sample constituents. This multi-step process allows for sequential operations to be performed on the sample, for example to capture microbes on the filter and subsequently wash or elute desired constituents from the filter.

Figure 4D:
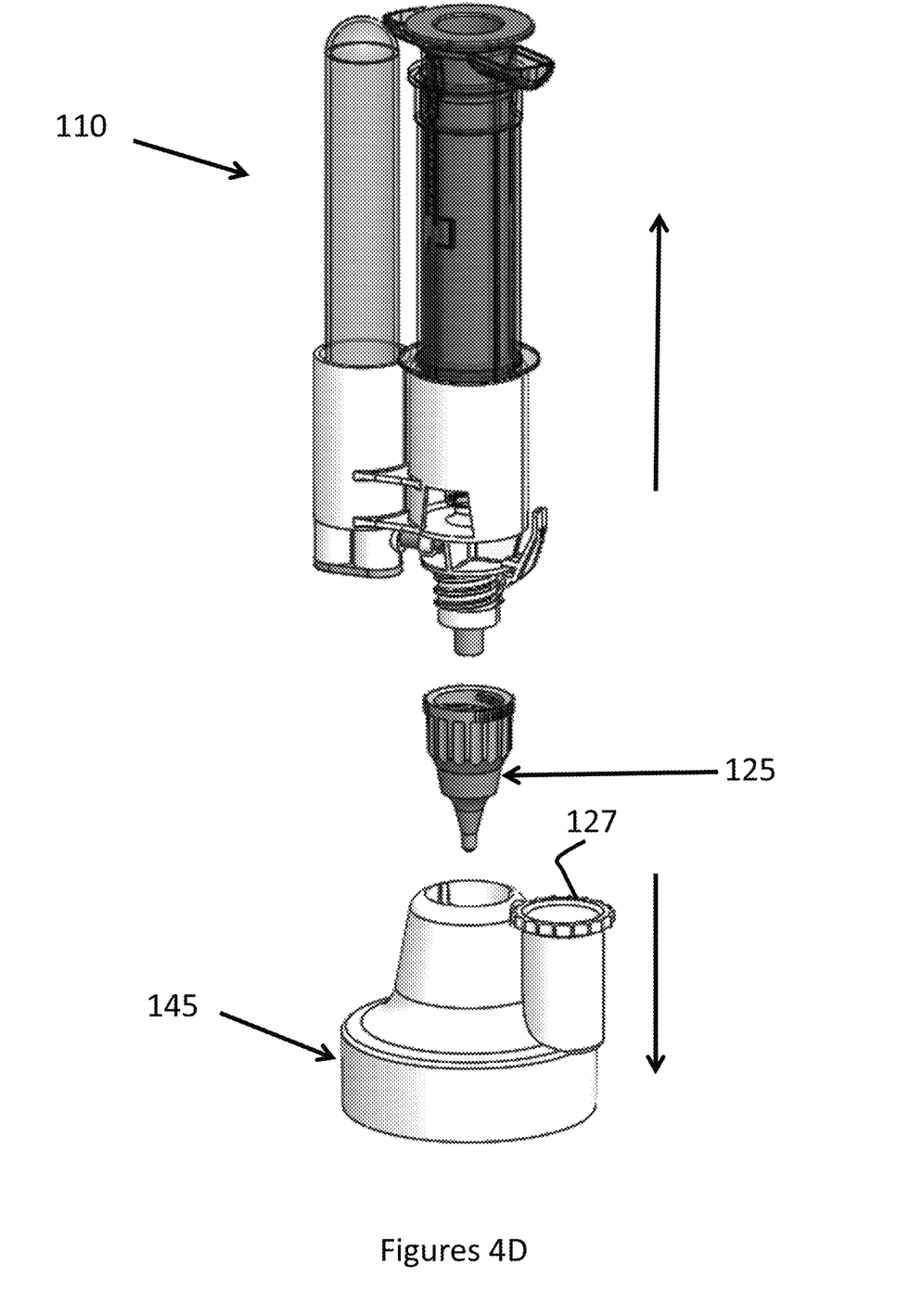
FIG. 4D illustrates certain components of an exemplary embodiment of the disclosure.

As shown in FIG. 4D, the sample processing assembly may be configured as separable subassemblies such that the sample tube retaining desired microbes or other constituents resultant from sample processing may be conveniently and quickly removed for further processing and/or analysis. In various embodiments, the components of the apparatus are fabricated from inexpensive materials and may be configured for single use or disposable. Additionally, the separable aspects of the apparatus aid in maintaining sterility and/or preventing contamination of the collected/retained material while reducing risk of exposure to the user.

The item 127 is an optional cap for the Sample Tube. The optional cap may contain the amplification reagent (under a foil seal that is punctured upon assembly), which may attach after the capture and wash process is completed and before the Sample Tube is transferred to the instrument.

An exemplary sample processing system that may be adapted for use with the apparatus and sample capture tube of the present disclosure for automated or semi-automated sample processing is described in commonly assigned PCT Application Serial PCT/US2013/075430 (Publication #WO2014093973) entitled "METHOD FOR CENTRIFUGE MOUNTABLE MANIFOLD FOR PROCESSING FLUIDIC ASSAYS" to John Nobile, the contents of which are hereby incorporated by reference in its entirety. It will be appreciated by those of skill in the art that the methods and apparatus of the present disclosure may be adapted to other platforms and configurations for sample processing and as such other embodiments and adaptations are considered within the scope of the present teachings.

The following examples are provided to further illustrate different embodiments of the disclosure. The examples are demonstrative and non-limiting in nature.

Example 1 is directed to an apparatus to capture pathogens from a biological sample, the apparatus comprising: a valve body to fluidically couple a sample tube to each of a syringe body and a capture tube, the valve body having a sample inlet, a first outlet, a second outlet, a channel to connect the sample inlet with each of the first and the second outlets, a first one-way valve to connect the sample inlet with the channel, a second one-way valve to connect the channel to the second outlet; a syringe body having an outer barrel and an inner barrel, the outer barrel further comprising a first reservoir containing a first reagent; and a plunger piston configured to moveably couple to the outer syringe barrel, the plunger piston comprising an inner syringe barrel, and outer syringe barrel and a puncture-able separator positioned between the first and second reservoirs, the inner syringe barrel defining a second reservoir to receive a second reagent; wherein the puncture-able separator is configured to provide automatic sequential delivery of the first and second reagents.

Example 2 is directed to the apparatus of example 1, wherein the valve body is configured to receive a sample tube and fluidically connect the sample to the inlet channel.

Example 3 is directed to the apparatus of example 2, wherein the valve body further comprises a piercing member configured to pierce the puncture-able separator to thereby access the second reagent.

Example 4 is directed to the apparatus of example 3, wherein the piercing member is configured to enter the second reservoir when the outer syringe, containing the first reagent, is nearly fully displaced, and the first reservoir is substantially empty.

Example 5 is directed to the apparatus of example 4, wherein the first and second reservoirs are separated by an elastomer diaphragm.

Example 6 is directed to the apparatus of example 2, wherein the valve body further comprises at least one inlet piercing member, the inlet piercing member configured to couple through the one-way valve to the sample tube.

Example 7 is directed to the apparatus of example 2, wherein the valve body further comprises a first and a second piercing members configured to enter the sample tube, the first piercing member to fluidically couple to the channel, the second piercing member to fluidically communicate with the ambient.

Example 8 is directed to the apparatus of example 7, wherein the second piercing member further comprises a one-way valve to allow ingress of ambient air into the sample tube.

Example 9 is directed to the apparatus of example 1, further comprising a capture tube to removably connect to the valve body, the capture tube having at least one filter membrane configured such that all fluids exiting the valve body pass through the at least one membrane.

Example 10 is directed to the apparatus of example 1, wherein the first one-way valve opens under a relative negative pressure on the syringe side of the valve and closes under a relative positive pressure on the syringe side of the valve.

Example 11 is directed to the apparatus of example 1, wherein the second one-way valve opens under a relative positive pressure on the syringe side of the valve, and closes under a relative negative pressure on the syringe side of the valve.

Example 12 is directed to a method to hermetically and sequentially mix a sample with a first processing fluid to form a first mixture and wash material captured from the first mixture with a second processing fluid, the method comprising: receiving a sample vessel containing a biological sample; applying a relative negative pressure to the sample vessel to transfer at least a portion of the sample from the sample vessel to the first reservoir, allowing a portion of the sample to admix with the first processing fluid to form the first mixture; applying an external relative positive pressure to the first reservoir by applying a pressure to the second processing fluid reservoir in physical communication with the first reservoir to expel a quantity of the first mixture from the first reservoir; and continuing to apply the external pressure, causing the second processing fluid to be released from the second reservoir.

Example 13 is directed to the method of example 12, wherein the step of applying an external positive pressure to the first reservoir further exerts the external positive pressure to the first admixture.

Example 14 is directed to the method of example 12, wherein continual application of external pressure delivers the second fluid by creating an opening in a barrier between the first and second reservoirs.

Example 15 is directed to the method of example 14, wherein the opening in the barrier places the second reservoir in fluidic communication only with a fluid exit channel which leads to a capture area.

Example 16 is directed to the method of example 12, further comprising filtering the first admixture through a membrane.

Example 17 is directed to the method of example 16, wherein the step of applying a relative negative pressure further comprises purging air from the first reservoir to substantially dry the membrane after the first admixture has passed through the membrane.

Example 18 is directed to method of example 12, wherein the sample defines biological fluid that may contain pathogens therein.

Example 19 relates to an apparatus to mix a sample with a pre-defined reagent, the apparatus comprising: a syringe body having an outer barrel and an inner barrel; a plunger piston configured to moveably couple to the syringe body, the plunger piston having a reservoir and a plunger gasket, the plunger gasket to sealingly couple the plunger piston with the inner barrel of the syringe, the plunger piston further having a reservoir to receive a second reagent; and a valve body to fluidically couple to the syringe body, the valve body having an inlet, a first outlet, a second outlet, a channel connecting the inlet with the first and the second outlets, a first one-way valve connecting the inlet with the channel and a second one-way valve connecting the channel to the second outlet.

Example 20 is directed to apparatus of example 19, wherein the outer barrel mates with the valve body through syringe coupler 115.

Example 21 is directed to the apparatus of example 19, wherein the valve body is configured to receive a sample tube and connect the sample tube to the inlet.

Example 22 is directed to the apparatus of example 19, wherein the plunger further comprises an auxiliary reservoir to receive a second processing fluid.

Example 23 is directed to the apparatus of example 22, wherein the valve body further comprises a piercing member to pierce the plunger gasket to thereby access the second reagent.

Example 24 is directed to the apparatus of example 22, wherein the piercing member is configured to extends to the auxiliary reservoir.

Example 25 is directed to the apparatus of example 22, wherein the plunger reservoir and the plunger auxiliary reservoir are separated by a diaphragm.

Example 26 is directed to the apparatus of example 21, wherein the valve body further comprises at least one inlet piercing member, the at least one inlet piercing member configured to couple the valve channel with the sample tube.

Example 27 is directed to the apparatus of example 19, further comprising a capture tube to connect the valve body to couple to the valve body, the capture tube having a filter membrane to capture at least one effluent from the second outlet of the valve body.

Example 28 is directed to the apparatus of example 19, wherein the first one-way valve opens under a relative negative pressure and closes under a relative positive pressure.

Example 29 is directed to the apparatus of example 19, wherein the second one-way valve closes under a relative negative pressure and closes under a relative positive pressure.

Example 30 is directed to a method to hermetically and sequentially mix a sample with a first processing fluid and a second processing fluid, the method comprising: receiving a sample quantity at a sample reservoir; receiving a quantity of the first processing fluid at a first reservoir and a quantity of the second processing fluid at a second reservoir, the first reservoir and the second reservoir fluidically separated by a gasket; pressurizing the sample reservoir to transfer at least a sample portion from the sample reservoir to the first reservoir and allowing the portion of the sample portion to admix with the first processing fluid to form a first mixture; exerting a first pressure on the first reservoir to expel a quantity of the first mixture from the first reservoir; exerting a second pressure on the first reservoir to introduce the second processing fluid to a portion of the first admixture to thereby form a second admixture; and exerting a third pressure on the first reservoir to expel a quantity of the second admixture.

Example 31 is directed to the method of example 30, wherein the first pressure is a relative negative pressure and the second pressure is a substantially positive pressure.

Example 32 is directed to the method of example 30, wherein the step of exerting a second pressure on the first reservoir to introduce the second processing fluid to a portion of the first admixture to thereby form a second admixture further comprises creating an opening in the gasket.

Example 33 is directed to the method of example 30, further comprising filtering the first admixture through a membrane.

Example 34 is directed to the method of example 33, wherein the step of exerting a first pressure on the first reservoir to expel a quantity of the first mixture from the first reservoir further comprises purging air from the first reservoir so as to substantially dry the membrane after the first admixture has passed through the membrane.

Example 35 is directed to the method of example 30, wherein the sample defines biological fluid having pathogens therein.

Example 36 is directed to the method of example 30, further comprising sealing the sample reservoir after the first pressure is ceased such that substantially no further sample is expelled from the first reservoir.

Example 37 is directed to the method of example 30, wherein the step of exerting a second pressure on the first reservoir to introduce the second processing fluid to a portion of the first admixture to thereby form a second admixture further comprises continuing exerting the second pressure to expel the first admixture from the second reservoir.

While the principles of the disclosure have been illustrated in relation to the exemplary embodiments shown herein, the principles of the disclosure are not limited thereto and include any modification, variation or permutation thereof.

What is claimed is:

1. An apparatus to capture pathogens from a biological sample, the apparatus comprising:
   a valve body (120) to fluidically couple a sample tube (130) to each of a syringe body (110, 4A) and a capture tube (135), the valve body (125) having a sample inlet, a first outlet, a second outlet, a channel to connect the sample inlet with each of the first and the second outlets, a first one-way valve (210) to connect the sample inlet with the channel, a second one-way valve (215) to connect the channel to the second outlet and a piercing member (225);
   a syringe body (110) having an outer barrel and an inner barrel, the outer barrel further comprising a first reservoir containing a first reagent; and
   a plunger piston configured to moveably couple to the outer syringe barrel, the plunger piston comprising an inner syringe barrel, and outer syringe barrel and a gasket between the first and second reservoirs, the inner syringe barrel defining a second reservoir to receive a second reagent.

2. The apparatus of claim 1, wherein the valve body is configured to receive a sample tube and fluidically connect the sample to the inlet channel.

3. The apparatus of claim 2, wherein the piercing member is configured to couple through the one-way valve to the sample tube.

4. The apparatus of claim 2, wherein the valve body further comprises a first and a second sample tube piercing members configured to enter the sample tube, the first sample tube piercing member to fluidically couple to the channel, the second sample tube piercing member to fluidically communicate with the ambient.

5. The apparatus of claim 4, wherein the second sample tube piercing member further comprises a one-way valve to allow ingress of ambient air into the sample tube.

6. The apparatus of claim 2, wherein the valve body further comprises a piercing member to pierce the gasket to thereby access the second reagent.

7. The apparatus of claim 6, wherein the piercing member is configured to enter the second reservoir when the outer syringe containing the first reagent is displaced and the first reservoir is substantially empty.

8. The apparatus of claim 7, wherein the gasket which separates the first and the second reservoirs is a diaphragm.

9. The apparatus of claim 1, further comprising a capture tube to removably connect to the valve body, the capture tube having at least one filter membrane configured such that all fluids exiting the valve body pass through the at least one membrane.

10. The apparatus of claim 1, wherein the first one-way valve opens under a relative negative pressure on the syringe side of the valve and closes under a relative positive pressure on the syringe side of the valve.

11. The apparatus of claim 1, wherein the second one-way valve opens under a relative positive pressure on the syringe side of the valve, and closes under a relative negative pressure on the syringe side of the valve.

12. The apparatus of claim 1, wherein the gasket provides automatic sequential delivery of the first and second reagents.

* * * * *